US009855684B2

(12) United States Patent
Ivory (10) Patent No.: US 9,855,684 B2
(45) Date of Patent: Jan. 2, 2018

(54) ELECTROPHORESIS SYSTEMS, DEVICES, AND ASSOCIATED METHODS OF ANALYSIS

(75) Inventor: Cornelius F. Ivory, Pullman, WA (US)

(73) Assignee: Washington State University, Pullman, WA (US)

(*) Notice: Subject to any disclaimer, the term of this patent is extended or adjusted under 35 U.S.C. 154(b) by 767 days.

(21) Appl. No.: 13/371,253

(22) Filed: Feb. 10, 2012

(65) Prior Publication Data

US 2013/0175170 A1 Jul. 11, 2013

Related U.S. Application Data

(60) Provisional application No. 61/584,532, filed on Jan. 9, 2012.

(51) Int. Cl.

| B29C 33/42 | (2006.01) |
| G01N 27/447 | (2006.01) |
| C08J 5/12 | (2006.01) |
| C09J 9/00 | (2006.01) |
| B29C 33/38 | (2006.01) |
| G03F 7/00 | (2006.01) |

(52) U.S. Cl.
CPC .......... *B29C 33/42* (2013.01); *B29C 33/3857* (2013.01); *C08J 5/122* (2013.01); *C09J 9/00* (2013.01); *G01N 27/44756* (2013.01); *G03F 7/0002* (2013.01); *C09J 2400/226* (2013.01); *Y10T 156/1039* (2015.01)

(58) Field of Classification Search
CPC .............. G01N 27/447–27/44752; G01N 27/44756–27/453; B01D 57/02; B81B 1/00–1/008; B29C 33/3857; B29C 33/42; C08J 5/122; C09J 9/00; C09J 2400/226; G03F 7/0002; Y10T 156/1039
USPC ................ 204/450–455, 549, 600–605, 645
See application file for complete search history.

(56) References Cited

U.S. PATENT DOCUMENTS

2011/0120867 A1* 5/2011 Mishina et al. .............. 204/451

FOREIGN PATENT DOCUMENTS

WO WO 2009025361 A1 * 2/2009

OTHER PUBLICATIONS

Slais, Model of isotachophoresis (displacement electrophoresis) in tapered capillaries, Electrophoresis, vol. 16, pp. 2060-2068 (1995).*

(Continued)

*Primary Examiner* — Luan V Van
*Assistant Examiner* — Maris R Kessel
(74) *Attorney, Agent, or Firm* — Liang IP, PLLC (57) ABSTRACT

Embodiments of electrophoresis systems, devices, and associated methods of analysis are described herein. In one embodiment, an electrophoresis device includes a first electrode having a first polarity, a second electrode having a second polarity, and a substrate. The substrate includes a first channel having a first section with a first cross-sectional area and a second section with a second cross-sectional area. The first end is electrically coupled to the first electrode, and the second end is electrically coupled to the second electrode. The first cross-sectional area is greater than the second cross-sectional area in a first dimension and in a second dimension generally orthogonal to the first dimension.

17 Claims, 8 Drawing Sheets

(56) References Cited

OTHER PUBLICATIONS

C. M. Brotherton and R. H. Davis, Electroosmotic flow in channels with step changes in zeta potential and cross section, Journal of Colloid and Interface Science, 270, (2004) pp. 242-246.*
Xiong, et al., "Base Stacking: pH-Mediated On-col. Sample Concentration for Capillary DNA Sequencing," Analytical Chemistry, vol. 70, No. 17, pp. 3605-3611, Sep. 1, 1998.
Xu, et al., "Room-Temperature Imprinting Method for Plastic Microchannel Fabrication," Analytical Chemistry, vol. 72, No. 8, pp. 1930-1933, Apr. 15, 2000.
Yussuf, et al., "Sealing of polymeric-microfluidic devices by using high frequency electromagnetic field and screen printing technique," Journal of Materials Processing Technology, 189, pp. 401-408, 2007.
Becker, Holger and Garnter, Claudia, "Polymer microfabrication methods for microfluidic analytical applications," Electrophoresis, 21, pp. 12-26, 2000.
Becker, Holger and Garnter, Claudia, "Polymer microfabrication technologies for microfluidic systems," Anal. Bioanal Chem, 390, pp. 89-111, 2008.
Chen, Yu-hung and Chen, Shu-Hui, "Analysis of DNA fragments by microchip electrophoresis fabricated on poly (methyl methacrylate) substrates using a wire-imprinting method," Electrophoresis, 21, pp. 165-170, 2000.
Chen et al., "Palladium Film Decoupler for Amperometric Detection in Electrophoresis Chips," Analytical Chemistry, vol. 73, No. 4, pp. 758-762, Feb. 15, 2001.
Del Campo et al., "Patterned Surfaces with Pillars with Controlled 3D Tip Geometry Mimicking Bioattachment Devices," Advanced Materials, 19, pp. 1973-1977, 2007.
Dolnik, et al., "Capillary electrophoresis on microchip," Electrophoresis, 21, pp. 41-54, 2000.
Duffy, et al., "Rapid Prototyping of Microfluidic Systems in Poly(dimethylsiloxane)," Analytical Chemistry, vol. 70, No. 23, pp. 4974-4984, Dec. 1, 1998.
El-Ali, et al., "Cells on chips," Nature Publishing Group, vol. 442, pp. 403-411, Jul. 27, 2006.
Esch, et al., "Influence of master fabrication techniques on the characteristics of embossed microfluidic channels," Lab Chip, 3, pp. 121-127, 2003.
Ferguson, et al., "Integrated Microfluidic Electrochemical DNA Sensor," Analytical Chemistry, vol. 81, No. 15, pp. 6503-6508, Aug. 1, 2009.
Fiorini, et al., "Fabrication of thermoset polyester microfluidic devices and embossing masters using rapid prototyped polydimethylsiloxane molds," Lab Chip, 3, pp. 158-163, 2003.
Fuentes, Herman V. and Woolley, Adam T., "Phase-Changing Sacrificial Layer Fabrication of Multilayer Polymer Mlcrofluidic Devices," Analytical Chemistry, vol. 80, No. 1, pp. 333-359, Jan. 1, 2008.
Kelly, et al., "Phase-Changing Sacrificial Materials for Solvent Bonding of High-Performance Polymeric Capillary Electrophoresis Microchips," Analytical Chemistry, vol. 77, No. 11, pp. 3536-3541, Jun. 1, 2005.
Koerner, et al., "Epoxy resins as stamps for hot embossing of microstructures and microfluidic channels," Sensors and Actuators B, 107, pp. 632-639, 2005.
Kraly, et al., "Review: Microfluidic applications in metabolomics and metabolic profiling," Analytica Chimica Acta 653, pp. 23-25, 2009.
Lion et al., "Microfludic Systems in Proteomics," Electrophoresis, 24, pp. 3533-3562, 2003.
Martynova, et al., "Fabrication of Plastic Microfluid Channels by Imprinting Methods," Analytical Chemistry, vol. 69, No. 23, pp. 4783-4789, Dec. 1, 1997.
McCormick, et al., "Microchannel Electrophoretic Separations of DNA in Injection-Molded Plastic Substrates," Analytical Chemistry, vol. 69, No. 14, pp. 2626-2630, Jul. 15, 1997.

Muck, et al., "Fabrication of Poly(methyl methacrylate) Microfluidic Chips by Atmospheric Molding," Analytical Chemistry, vol. 76, No. 8, Apr. 15, 2004.
Narasimhan, Jagannathan and Papautsky, Ian, "Polymer embossing tools for rapid protyping of plastic microfluidic devices," Journal of Micromechanics and Microengineering, 14, 96, 9 pages, 2004.
Pamme, Nicole, "Continuous flow separations in microfluidic devices," Lab Chip, 7, pp. 1644-1659, 2007.
Mairhofer, et al., "Microfluidic Systems for Pathogen Sensing: A Review," Sensors, 9, pp. 4804-4823, Jun. 17, 2009.
Sabounchi, et al., "Sample concentration and impedance detection on a microfluidic polymer chip," Biomed Microdevices, 10, pp. 661-670, May 17, 2008.
Shadpour, et al., "Physiochemical properties of various polymer substrates and their effects on microchip electrophoresis performance," Journal of Chromatography A, 1111, pp. 238-251, 2006.
Szantai, Eszter and Guttman, Andras, "Genotyping with microfluidic devices," Electrophoresis, 27, pp. 4896-4903, 2006.
Tsao, Chia-Wen and Devoe, Don L., "Bonding of thermoplastic polymer microfluidics," Microfluid Nanofluid, 6, pp. 1-16, 2009.
Wang, Shau-Chun and Morris, Michael, D., "Plastic Microchip Electrophoresis with Analyte Velocity Modulation Application to Fluorescence Background Rejection," Analytical Chemistry, vol. 72, No. 7, pp. 1448-1452, Apr. 1, 2000.
An et al., "Selective enrichment and ultrasensitive identification of trace peptides in proteome analysis using transient capillary isotachophoresislzone electrophoresis coupled with nano-ESI-MS," Electrophoresis, 27, pp. 3599-3608, 2006.
Belligundu, Sunil and Shiakolas, Panayiotis S., "Study on two-stage hot embossing microreplication: silicon to polymer to polymer," J. Microlith, Microfab., Microsyst, 5(2), 021103, pp. 1537-1646, Apr.-Jun. 2007.
Chen, et al., "Fabrication and characterizatoin of poly(methyl methacrylate) microchannels by in situ polymerization with a novel metal template," Electrophoresis, 24, pp. 3246-3252, 2003.
Chen et al., "Fabrication of poly(methyl methacrylate) microfluidic chips by redox-initiated polymerization," Electrophoresis, 28, pp. 2897-2903, 2007.
Chen, et al., "Fabrication, modification, and application of poly(methyl methacrylate) microfluidic chips," Electrophoresis, 29, pp. 1801-1814, 2008.
Chen, et al.,"Fabrication of PMMA CE microchips by infrared-assisted polymerization," Electrophoresis 29, pp. 4922-4927, 2008.
Das, Champak and Fan, Z. Hugh, "Effects of separation length and voltage on isoelectric focusing in a plastic microfluidic device," Electrophoresis 27, pp. 3619-3626, 2006.
Davis, et al., "Capillary and Microfludic Gradient Elution Isotachophoresis Coupled to Capillary Zone Electrophoresis for Femtomolar Amino Acid Detection Limits," Analytical Chemistry, vol. 81, No. 13, pp. 5452-5459, Jul. 1, 2009.
Dittrich, Petra S. and Manz, Andreas, "Lab-on-a-chip: microfluidics in drug discovery," vol. 5, Nature Publishing Group, pp. 210-218, Reviews, Nature Publishing Group, Mar. 2006.
Fang, et al., "Application of capillary isotachophoresis-based multidimensional separations coupled with electrospray ionizaton-tandem mass spectrometry for characterization of mouse brain mitochondrial proteome," Electrophoresis, vol. 29, pp. 2215-2223, 2008.
Harrison, et al., "Micromachining a Miniaturized Capillary Electrophoresis-Based Chemical Analysis System on a Chip," American Association for the Advancement of Science, vol. 261, No. 5123, pp. 895-897, Aug. 13, 1993.
Hirokawa, et al., "Analysis of a dilute sample by capillary zone electrophoresis with isotachophoretic preconcentration," Journal of Chromatography, vol. 634, Issue 1, pp. 101-106, 1993.
Hsu, Yi-Chu and Chen, Tang-Yuan, "Applying Taguchi methods for solvent-assisted PMMA bonding technique for static and dynamic-TAS devices, " Biomed Microdevices, vol. 9, pp. 513-522, 2007.
Kim, Joohan and Xu, Xianfan, "Excimer laser fabrication of polymer microfluidic devices," Journal of Laser Applicatons, vol. 15, No. 4, pp. 255-260, Nov. 2003.

(56) References Cited

OTHER PUBLICATIONS

Koesdjojo, et al., "Fabrication of a Microfluidic System for Capillary Electrophoresis Using a Two-Stage Embossing Technique and Solvent Welding on Poly(methyl methaciylate) with Water as a Sacrificial Layer," Analytical Chemistry, vol. 80, No., 7, pp. 2311-2318, Apr. 1, 2008.
Liu, et al., "Isotachophoresis preconcentration integrated microfluidic chip for highly sensitive genotyping of the hepatitis B virus," Journal of Chromatography B, vol. 844, pp. 32-38, 2006.
Liu, et al., "Double-column fixation for type C fractures of the distal humerus in the elderly," Journal of Shoulder and Elbow Surgery, 18, pp. 646-651, 2009.
Lu, et al., "Packaging of Microfluidic Chips via Interstitial Bonding Technique," Research Express@NCKU, vol. 9, Issue 7, 5 pages, Jul. 10, 2009.
Manz, et al., "Planar chips technology for miniaturization and integration of separation techniques into monitoring systems," Journal of Chromatography, 593, pp. 253-258, 1992.
Qi, et al., "Microfluidic devices fabricated in poly(methyl methacrylate) using hot-embossing with integrated sampling capillary and fiber optics for fluorescence detection," Lab Chip, 2, pp. 88-95, Mar. 28, 2002.
Qu, et al., "Poly(methyl methacrylate) CE microchips replicated from poly(dimethylsiloxane) templates for the determination of cations," Electrophoresis 27, pp. 4910-4918, 2006.
Xia, Younan and Whitesides, George M., "Soft Lithography," Annu. Rev. Mater. Sci. 28, pp. 153-184, 1998.
Xu, et al, "Fabrication of poly(methyl methacrylate) capillary electrophoresis microchips by in situ surface polymerization," Lab Chip, 6, pp. 145-148, 2006.
Xu, et al., "Sensitive profiling of biogenic amines in urine using CE with transient isotachophoretic preconcentration," J. Sep. Sci., 32, pp. 4143-4147, 2009.
Yan, et al., "In-line preconcentration of oxidized and reduced glutathione in capillary zone electrophoresis using transient isotachophoresis under strong counter-electroosmotic flow," Journal of Chromatography A, 1216, pp. 8665-8670, 2009.
Zhu, et al., "Study of PMMA thermal bonding," Microsyst Technol. 13, pp. 403-407, 2007.
Becker, Holger and Locascio, Laurie, E., "Polymer microfluidic devices," Talanta 56, pp. 267-287, 2002.
Brister, C. Paul and Weston, Kenneth, D., "Patterned Solvent Delivery and Etching for the Fabrication of Plastic Microfluidic Devices," Analytical Chemistry, vol. 77, No. 22, pp. 7478-7482, Nov. 15, 2005.
Brown, et al., "Fabrication and characterization of poly(methylmethacrylate) microfluidic devices bonded using surface modifications and solvents," Lab Chip, 6, pp. 66-73, 2006.
Brown, Robert B. and Audet, Julie, "Sampling Efficiency of a Single-Cell Capillary Electrophoresis System," Cytometry Part A, 71A, pp. 882-888, 2007.
Cheng, et al., "Direct-write laser micromachining and universal surface modification of PMMA for device development," Sensors and Actuators B, 99, pp. 186-196, 2004.
Cui, et al., "Isoelectric Focusing in a Poly(dimethylsiloxane) Microfluidic Chip," Analytical Chemistry, vol. 77, No. 5, pp. 1303-1309, Mar. 1, 2005.
Cui, et al., "Isotachophoresis of proteins in a networked microfluidic chip: Experiment and 2-D simulation," Electrophoresis, 28, pp. 1138-1145, 2007.
Cui, et al., "Automated Electric Valve for Electrokinetic Separation in a Networked Microfluidic Chip," Analytical Chemistry, vol. 79, No. 4, pp. 1456-1465, Feb. 15, 2007.
Kelly, Ryan T. and Woolley, Adam, T., "Thermal Bonding of Polymeric Capillary Electrophoresis Microdevices in Water," Analytical Chemistry, vol. 75, No. 8, pp. 1941-1945, Apr. 15, 2003.
Klank, et al., "Co2-laser micromachining and back-end processing for rapid production of PMMA-based microfluidic systems," Lab Chip, 2, pp. 242-246, 2002.
Koesdjojo, et al., "Techniques for Microfabrication of Polymeric-Based Microchips from an SU-8 Master with Temperature-Assisted Vaporized Organic Solvent Bonding," Analytical Chemistry, vol. 81, No. 4, pp. 1652-1659, Feb. 15, 2009.
Kaniansky, et al., "Capillary Electrophoresis Separations on a Planar Chip with the Column-Coupling Configuration of the Separation Channels," Analytical Chemistry, vol. 72, No. 15, pp. 3596-3604, Aug. 1, 2000.
Krivankova, Ludmila and Bocek, Petr, "Synergism of capillary isotachophoresis and capillary zone electrophoresis," Journal of Chromatography B, 689, pp. 13-34, 1997.
Lei, et al., "Microwave bonding of polymer-based substrates for potential encapsulated microlnanofluidic device fabrication," Sensors and Actuators A 114, pp. 340-346, 2004.
Mair, et al., "Room-Temperature Bonding for Plastic High-Pressure Microfluidic Chips," Analytical Chemistry, vol. 79, No. 13, pp. 5097-5102, Jul. 1, 2007.
Metwalli, et al., "Surface characterizations of mono-, di-, and tri-aminosilane treated glass substrates," Journal of Colloid and Interface Science, 298, pp. 825-831, 2006.
Ng, et al., "Thermally activated solvent bonding of polymers," Microsyst Technol. 14, pp. 753-759, 2008.
Peeni, et al., "Sacrificial layer microfluidic device fabrication methods," Electrophoresis, 27, pp. 4888-4895, 2006.
Shah, et al., "Capillarity Induced Solvent-Actuated Bonding of Polymeric Microfluidic Devices," Analytical Chemistry, vol. 78, No. 10, pp. 3348-3353, May 15, 2006.
Sun et al., "Rapid prototyping of poly(methyl methacrylate) microfluidic systems using solvent imprinting and bonding," Journal of Chromatography A, 1162, pp. 162-166, 2007.
Truckenmuller, et al., "Micro ultrasonic welding: joining of chemically inert polymer microparts for single material fluidic components and systems," Microsyst Technol. 12, pp. 1027-1029, 2006.
Urbanek, et al., "Determination of trace cationic impurities in butylmethylimidazolium-based ionic liquids: From transient to comprehensive single-capillary counterflow isotachophoresis-zone electrophoresis," Electrophoresis, 27, pp. 4859-4871, 2006.
Vreeland, et al., "Tandem Isotachophoresis-Zone Electgrophoresis via Base-Mediated Destacking for Increased Detection Sensitivity in Microfluidic Systems," Analytical Chemistry, vol. 75, No. 13, pp. 3059-3065, Jul. 1, 2003.
Wainright, et al., "Sample pre-concentration by isotachophoresis in microfluidic devices," Journal of Chromatography A, 979, pp. 69-80, 2002.
Office Action in U.S. Appl. No. 13/445,228 dated Jul. 17, 2014, 16 pages.
Emrich, et al. "Microfabricated Two-Dimensional Electrophoresis Device for Differential Protein Expression Profiling", Analytical Chemistry, vol. 79, No. 19, Oct. 2007, p. 7360-7366.
Jubery, et al. "Preconcentration of Cardiac Proteins in a Microfluidic Device", Paper IMECE2009-10772; vol. 12, Part B, Micro and Nano Systems, Proceedings of the ASME 2009 International Mechanical Engineering Congress & Exposition, Nov. 13-19, 2009, p. 613-617.
Bottenus, et al. "Preconcentration and detection of the phosphorylated forms of cardiac troponin I in a cascade microchip by cationic isotachophoresis", Lab on a Chip, vol. 11, No. 22, Nov. 2011, p. 3793-3801.
Office Action in U.S. Appl. No. 13/371,265 dated Nov. 14, 2014, 13 pages.
Ng S. H., Tjeung R. T., Wang Z. F., Lu A. C. W., Rodriguez 1., de Rooij N. F. (2007) Thermally activated solvent bonding of polymers. Microsyst Technol14:753-759.
Notice of Allowance in U.S. Appl. No. 13/445,228 dated Nov. 21, 2014, 8 pages.
Office Action in U.S. Appl. No. 13/371,265 dated Jun. 19, 2015, 19 pages.
Tsao, Chia-Wen and DeVoe, Don L. (2009) Bonding of thermoplastic polymer microfluidics. Microfluid. Nanofluid. 6: 1-16.
Koenig, Jack L. and Miller-Chou, Beth A. (2003) A review of polymer dissolution. Prog. Polym. Sci. 28: 1223-1270.

* cited by examiner

ELECTROPHORESIS SYSTEMS, DEVICES, AND ASSOCIATED METHODS OF ANALYSIS

CROSS-REFERENCE TO RELATED APPLICATION(S)

This application claims priority to U.S. Provisional Application No. 61/584,532, filed on Jan. 9, 2012.

BACKGROUND

Analyzing samples with dilute components can be a useful technique in analytical chemistry, medical science, and other technology fields. However, separating or even detecting components with low concentrations can be challenging. For example, cardiac troponin I (cTnI) is a biomarker useful for diagnosing patients for myocardial injury. In particular, it is believed that a ratio between phosphorylated and unphosphorylated cTnI can be a good indicator of a patient's risk of suffering myocardial damage.

However, cTnI levels in healthy people are often lower than detection limits of conventional diagnostic techniques. Though assays (e.g., i-STAT provided by Abbott Diagnostics of Abbott Park, Ill.) have been developed to detect cTnI, such assays can only measure total cTnI content and do not distinguish between phosphorylated and unphosphorylated cTnI. Other conventional analysis techniques for cTnI include non-equilibrium isoelectric focusing, mass spectrometry, and phosphate-affinity sodium dodecyl sulfate polyacrylamide gel electrophoresis ("SDS-PAGE"). These techniques, however, have long test time and low sample throughput.

DETAILED DESCRIPTION

Various embodiments of electrophoresis systems, devices, and associated methods of analysis are described below. As used herein, the term "electrophoresis" or "cataphoresis" generally refers to separating electrically charged particles in a sample based on mobility of the particles relative to a fluid under the influence of an electric field. Without being bound by theory, it is believed that different charged particles can migrate at different speeds (commonly referred to as electrophoretic mobility) relative to a fluid in an electric field. The charged particles may have different charge polarity, charge state, particle size, and/or other characteristics. As a result, the charged particles separate from one another during migration in the fluid (e.g., a solvent or buffer solution). The separated charged particles may then be collected and further analyzed for identification and/or abundance. The term "microchannel" generally refers to a channel with a hydraulic diameter below about 1 millimeter.

Also used herein, the term "isotachophoresis" ("ITP") generally refers to an electrophoresis technique in which a sample is introduced between a leading electrolyte ("LE") and a terminating electrolyte ("TE") before an electrical field is applied. The LE has an electrophoretic mobility greater than any charge particles of interest in the sample. The TE has an electrophoretic mobility lower than any charge particles of interest in the sample. After an electric field is applied, charge particles in the sample separate from one other while the sample is moving along with and between the LE and TE in a channel. After reaching corresponding equilibrium concentrations (i.e., in peak mode), the separated charged particles form distinct volumes or "stacks" in the channel with sharp boundaries between adjacent stacks.

As discussed above in the Background section, detecting low concentration components of a sample can be challenging. The inventor has recognized that by applying ITP in a microchannel with cross-sectional area reductions, low concentration components (e.g., phosphorylated and un-phosphorylated cTnI) can be separated and substantially concentrated (e.g., by a factor of about 10,000). As a result, embodiments of the present technology can lower detection limits, increase analysis sensitivity, and decrease analysis costs when compared to conventional analysis techniques. Certain embodiments of analysis systems, devices, and methods of analysis in accordance with the present technology are discussed below. However, a person skilled in the relevant art will understand that the technology may have additional embodiments, and that the technology may be practiced without several of the details of the embodiments described below with reference to FIGS. 1A-8.

Figure 1A:
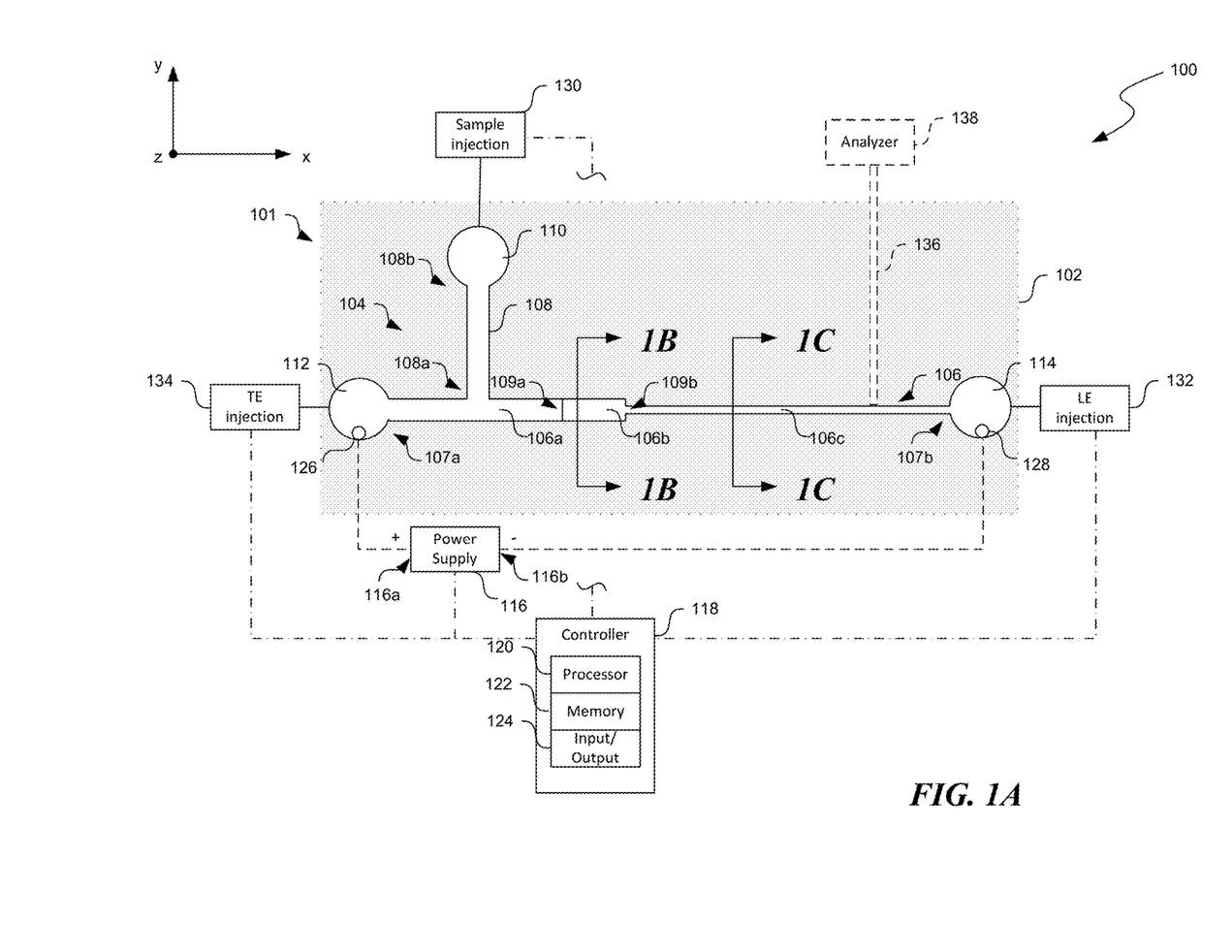
FIG. 1A is a partially schematic diagram of an analysis system in accordance with embodiments of the present technology.

FIG. 1A is a partially schematic diagram of an analysis system 100 in accordance with embodiments of the present technology. As shown in FIG. 1A, the analysis system 100 can include an electrophoresis device 101 in fluid communication with a sample injection device 130, an LE injection device 132, and a TE injection device 134 (collectively referred to as "injection devices"). The injection devices can include a syringe, a pump, and/or other suitable devices configured to supply a fluid to the electrophoresis device 101. Optionally, in certain embodiments, the analysis system 100 can include also an analyzer 138 in fluid communication with the electrophoresis device 101 via an output conduit 136. For example, the analyzer 138 can include an immuneaffinity assay, a capillary-zone electrophoresis analyzer, an optical analyzer, a spectroscopic analyzer, an isoelectric focusing analyzer, a gel electrophoresis analyzer, a mass spectrometry analyzer, an SDS-PAGE analyzer, and/or other suitable types of analyzer. In other embodiments, the analyzer 138 may be incorporated into the electrophoresis device 101. In further embodiments, the analyzer 138 may be omitted.

As shown in FIG. 1A, the electrophoresis device 101 can include a substrate 102 (shown in phantom lines for clarity) having a passage 104 in fluid communication with a sample reservoir 110, a TE reservoir 112, and an LE reservoir 114 (collectively referred to as "reservoirs"). In certain embodiments, the electrophoresis device 101 can also include a cover (not shown) configured to enclose the passage 104 in the substrate 102. For example, in certain embodiments, the cover can include a generally flat plate securely fastened to the substrate 102 with glue, mechanical fasteners, welding materials, and/or other suitable fasteners. In other embodiments, the cover can be generally similar to the configuration of the substrate 102. In further embodiments, the cover may be omitted, and the passage 104 may be embedded in the substrate 102.

In the illustrated embodiment, the substrate 102 includes a plate or "chip" constructed from poly(methyl methacrylate) ("PMMA"). In other embodiments, the substrate 102 can be constructed with glass, silicon, metals, ceramics, and/or other suitable substrate materials. In certain embodiments, the reservoirs can individually include an aperture, indentation, and/or other suitable space in the substrate 102 and/or cover. In other embodiments, the reservoirs can individually include a container and/or other suitable fluid holder external to the substrate 102.

As shown in FIG. 1A, in the illustrated embodiment, the passage 104 includes a first channel 106 generally perpendicular to and in fluid communication with a second channel 108. The first channel 106 includes a first section 106a, a second section 106b, and a third section 106c arranged in series between a first end 107a and a second end 107b. The first channel 106 is coupled to the TE reservoir 112 at the first end 107a and to the LE reservoir 114 at the second end 107b. The second channel 108 includes a first end 108a coupled to the first section 106a of the first channel 106 and a second end 108b coupled to the sample reservoir 110.

Figure 1B:
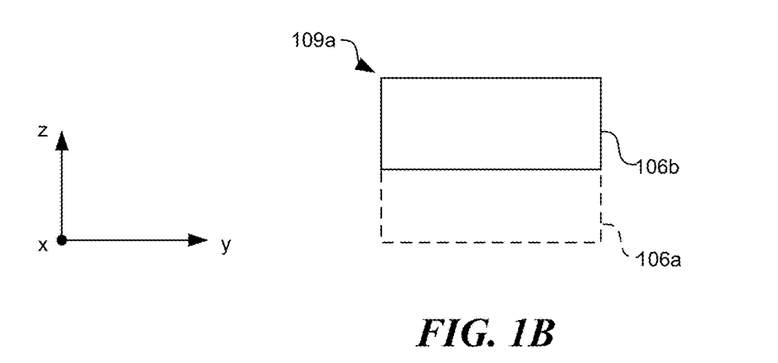
FIGS. 1B and 1C are cross-sectional views of a portion of the electrophoresis device in FIG. 1A in accordance with embodiments of the present technology.
Figure 1C:
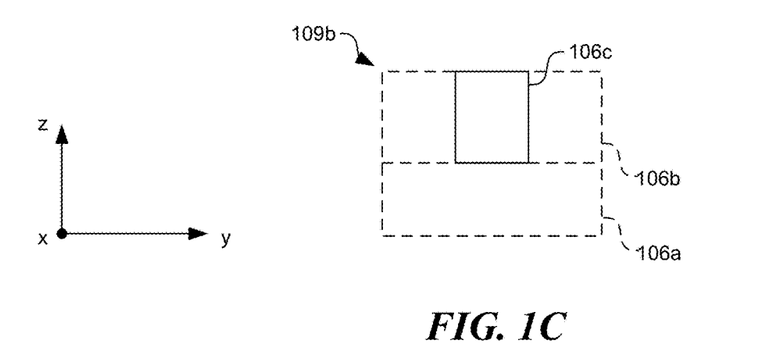

The first channel 106 can include one or more constrictions along the x-dimension. As used herein, the term "constriction" generally refers to a reduction in cross-sectional area along a flow direction. For example, as shown in FIG. 1B, the first section 106a of the first channel 106 has a cross-sectional area that is larger than the second section 106b in a first dimension (e.g., the z-dimension) to form a first constriction 109a. As shown in FIG. 1C, the second section 106b has a cross-sectional area larger than the third section 106c generally in a second dimension (e.g., the y-dimension) to form a second constriction 109b. The first dimension is generally perpendicular or orthogonal to the second dimension.

The cross-sectional area reduction across the first and/or second constrictions 109a and 109b can be by a factor of 2, 3, 4, 5, 10, 100, and/or other suitable values. In certain embodiments, the first and second constrictions 109a and 109b can have the same reduction factor (e.g., 10). In other embodiments, the first and second constrictions 109a and 109b can have different reduction factors. Even though particular configuration of first and second constrictions 109a and 109b is shown in FIGS. 1A-1C, in other embodiments, the electrophoresis device 101 may include other passage configurations, as discussed in more detail below with reference to FIGS. 2-5C.

Referring back to FIG. 1A, the analysis system 100 can also include a power supply 116 electrically coupled to a first electrode 126 and a second electrode 128. The power supply 116 can include a direct current source, a transformer, a rectifier, and/or other suitable electrical components configured to supply a voltage to the first and second electrodes 126 and 128. In the illustrated embodiment, the first electrode 126 is coupled to a cathode 116a, and the second electrode 128 is coupled to an anode 116b of the power supply 116. In other embodiments, the power supply 116 can have opposite and/or different polarity arrangements.

The first and second electrodes 126 and 128 can include platinum, gold, and/or other suitable types of electrodes. In the illustrated embodiment, the first and second electrodes 126 and 128 are placed in the TE reservoir 122 and the LE reservoir 124, respectively. In other embodiments, the first and second electrodes 126 and 128 can be spaced apart from but electrically coupled to the TE reservoir 122 and the LE reservoir 124, respectively. In further embodiments, the first and second electrodes 126 and 128 can have other suitable configurations.

The analysis system 100 can also include a controller 118 operatively coupled to components of the analysis system 100 for controlling operation of the analysis system 100. The controller 118 can include a processor 120 coupled to a memory 122 and an input/output component 124. The processor 120 can include a microprocessor, a field-programmable gate array, and/or other suitable logic devices. The memory 122 can include volatile and/or nonvolatile computer readable media (e.g., ROM; RAM, magnetic disk storage media; optical storage media; flash memory devices, EEPROM, and/or other suitable non-transitory storage media) configured to store data received from, as well as instructions for, the processor 120. The input/output component 124 can include a display, a touch screen, a keyboard, a track ball, a gauge or dial, and/or other suitable types of input/output devices configured to accept input from and/or provide output to an operator.

In certain embodiments, the controller 118 can include a computer operatively coupled to the other components of the analysis system 100 via a hardwire communication link (e.g., a USB link, an Ethernet link, an RS232 link, etc.). In other embodiments, the controller 118 can include a logic processor operatively coupled to the other components of the analysis system 100 via a wireless connection (e.g., a WIFI link, a Bluetooth link, etc.). In further embodiments, the controller 118 can include an application specific integrated circuit, a system-on-chip circuit, a programmable logic controller, and/or other suitable computing frameworks.

In operation, the controller 118 can cause the LE injection device 132 to inject an LE carried by a fluid (e.g., a buffer solution) into the LE reservoir 114 and the first channel 106 until the injected fluid substantially fills the first and second channels 106 and 108. Subsequently, the controller 118 can cause the sample injection device 130 to inject a sample (e.g., a blood sample) into the sample reservoir 110. The injected sample can then substantially fill the first section 106a of the first channel 106 and the TE reservoir 112 by displacing a portion of the LE. Then, the controller 118 can cause the TE injection device 134 to inject a TE into the TE reservoir 112.

The controller 118 can then issue instructions to the power supply 116 to supply a voltage to the first and second electrodes 126 and 128. Under the influence of the applied voltage, the LE, sample, and TE migrate along the x-dimension in the first channel 106. As a result, components of the sample are separated by ITP to form distinctive stacks based on electrophoretic mobility of individual components.

As shown in FIG. 1A, the applied voltage also forces the migrating sample to flow through the first constriction 109a and the second constriction 109b while components of the sample are separated by ITP. The inventor has recognized that by forcing the sample to flow through the first and second constrictions 109a and 109b, components of the sample can be substantially concentrated. Without being bound by theory, it is believed that as the cross-sectional area of the first channel 106 is decreased, concentrations of sample components can be increased proportionally as follows:

$$c_i = \frac{M_i}{w_i A} \quad \text{Equation 1}$$

where $c_i$ is the concentration of a sample component i, $M_i$ is a total mass or molar load of component i, $w_i$ is a peak width of species i, and A is a cross-sectional area of the first channel 106. As shown in Equation 1, the concentration of a sample component $c_i$ is inversely proportional to the cross-sectional area A of the first channel 106. As a result, a reduction in the cross-sectional area A of the first channel 106 can result in an increase in the concentration of the sample component $c_i$.

However, one difficulty of significantly reducing the cross-sectional area of a channel is structural stability. For example, the inventor has discovered that if the cross-sectional area of the first channel 106 is reduced only in one dimension, the walls in the first channel 106 would cave in before a significant reduction (e.g., by a factor of 20) can be achieved in a PMMA substrate 102. To overcome the foregoing difficulty, the inventor recognized that by reducing the cross-sectional area of the first channel 106 in two dimensions, significant reductions may be achieved without compromising the structural stability of the passage 104. For example, the first constriction 109a can have a reduction factor of 5, and the second constriction 109b can have a reduction factor of 10. Thus, the first and second constrictions 109a and 109b can have a combined cross-sectional area reduction factor of 50. As a result, forcing the sample to flow through both the first and second constrictions 109a and 109b can result in a concentration increase by a factor of 50.

The separated and concentrated sample components (e.g., phosphorylated and unphosphorylated cTnI) can then be collected by the analyzer 138 via the output conduit 136. The analyzer 138 may then determine at least one of an identity and concentration of the sample components. Original concentrations of the sample components may then be calculated based on Equation 1. Even though the operation of the analysis system 100 is described above from the perspective of the controller 118, in other embodiments, the analysis system 100 may be operated by an operator with or without utilizing the controller 118 and/or other components of the analysis system 100.

Figure 2:
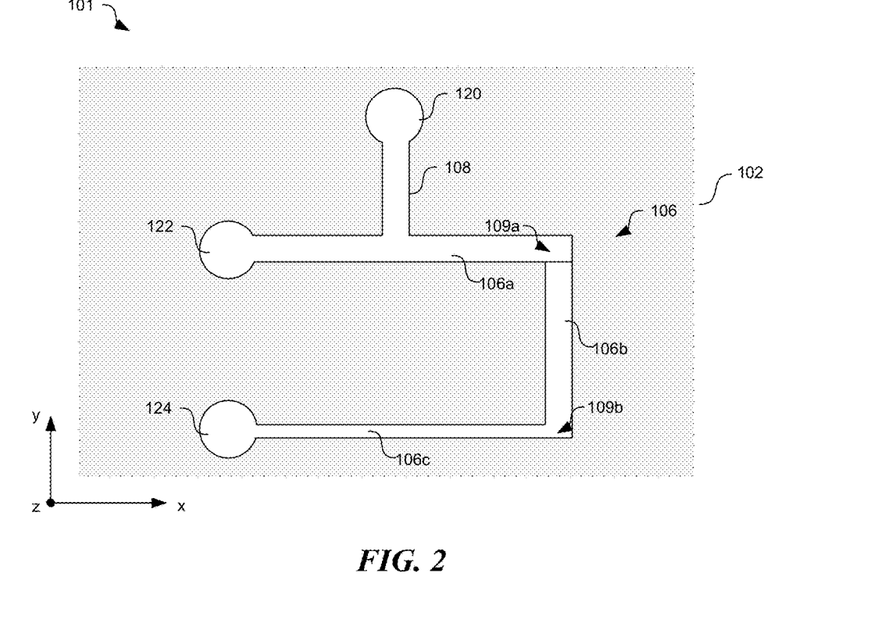
FIG. 2 is a plan view of an electrophoresis device suitable for the analysis system in FIG. 1A in accordance with embodiments of the present technology.

The electrophoresis device 101 shown in FIG. 1A has a generally linear first channel 106. In other embodiments, the electrophoresis device 101 can also include non-linear channels. For example, FIG. 2 is a plan view of another electrophoresis device 101 suitable for the analysis system in FIG. 1A in accordance with embodiments of the present technology. As shown in FIG. 2, the electrophoresis device 101 can include generally similar components as that in FIG. 1A except that the first section 106a, the second section 106b, and the third section 106c of the first channel 106 are arranged generally in a "U" shape. In other embodiments, sections of the first channel 106 can also form a "Z" shape, an "L" shape, or other suitable shapes.

Figure 3A:
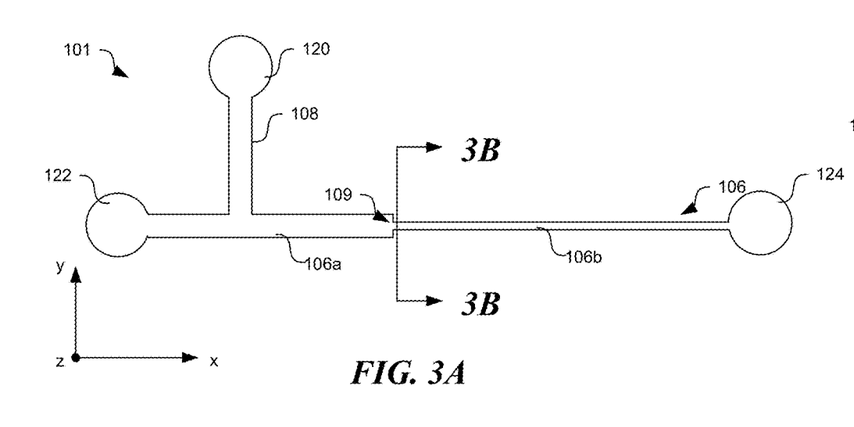
FIG. 3A is a plan view of another electrophoresis device suitable for the analysis system in FIG. 1A in accordance with embodiments of the present technology.
Figure 3B:
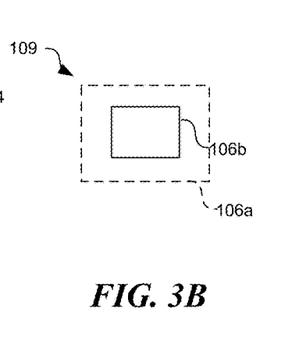
FIG. 3B is a cross-sectional view of a portion of the electrophoresis device in FIG. 3A in accordance with embodiments of the present technology.
Figure 4A:
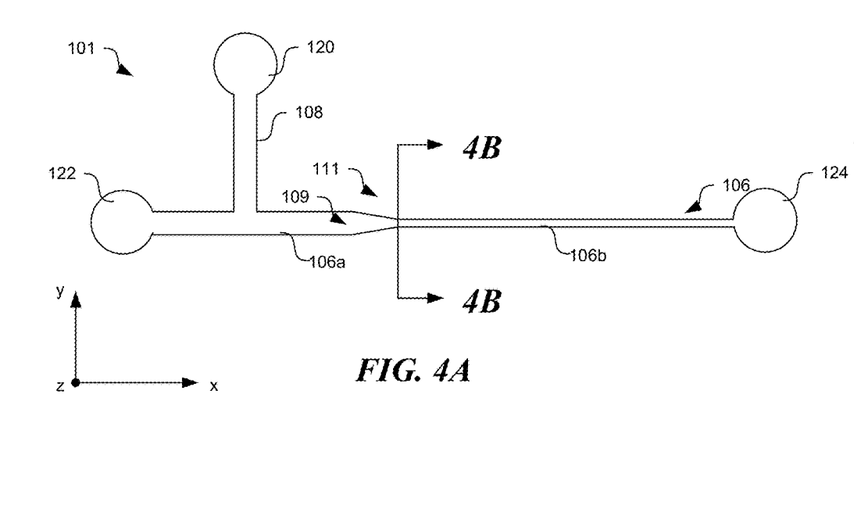
FIG. 4A is a plan view of another electrophoresis device suitable for the analysis system in FIG. 1A in accordance with embodiments of the present technology.
Figure 4B:
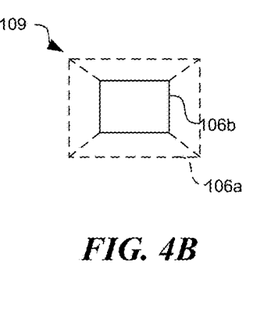
FIG. 4B is a cross-sectional view of a portion of the electrophoresis device in FIG. 4A in accordance with embodiments of the present technology.

Even though the first channel 106 in FIGS. 1A-2 is shown to have consecutive and discrete reductions in cross-sectional area, in other embodiments, the first channel 106 can also have a single two-dimensional reduction in cross-sectional area. FIG. 3A is a plan view and FIG. 3B is a cross-sectional view of another electrophoresis device 101 suitable for the analysis system 100 in FIG. 1A in accordance with embodiments of the present technology. In FIGS. 3A and 3B and in other figures, certain components of the electrophoresis device 101 are omitted for clarity. As shown in FIGS. 3A and 3B, in certain embodiments, the electrophoresis device 101 includes a single constriction 109 with a reduction in cross-sectional area in both the z-dimension and the y-dimension. As a result, the second section 106b can be generally concentric to the first section 106a. FIG. 4A is a plan view and FIG. 4B is a cross-sectional view of another electrophoresis device 101 with a single constriction 109 except that the first channel 106 includes a tapered portion 111 between the first section 106a and the second section 106b.

Figure 5A:
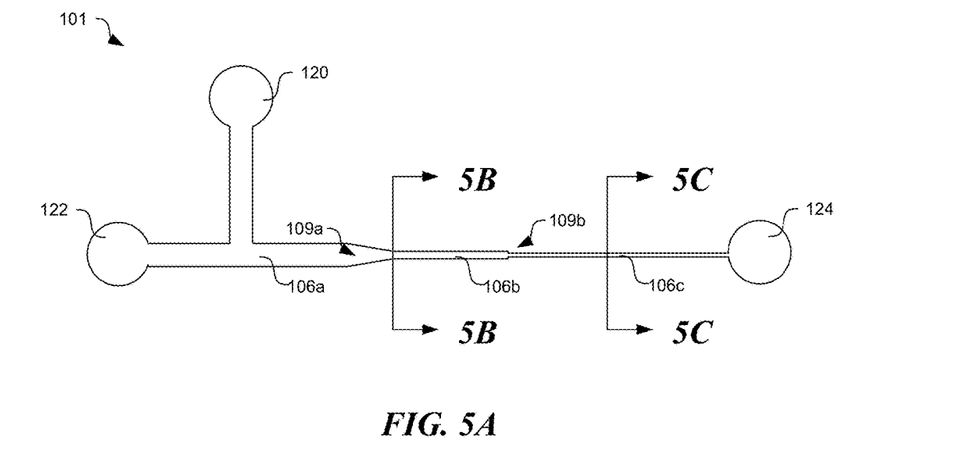
FIG. 5A is a plan view of another electrophoresis device suitable for the analysis system in FIG. 1A in accordance with embodiments of the present technology.
Figure 5B:
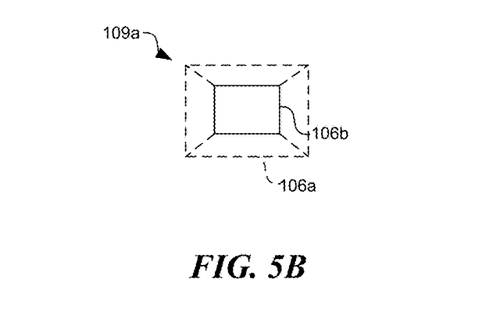
FIGS. 5B and 5C are cross-sectional views of a portion of the electrophoresis device in FIG. 5A in accordance with embodiments of the present technology.
Figure 5C:
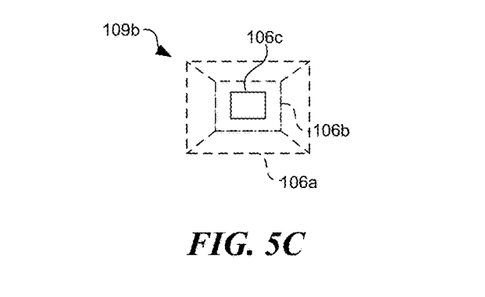

In other embodiments, the electrophoresis device 101 can also include a plurality of constrictions individually having two-dimensional reduction in cross-sectional area. For example, FIG. 5A is a plan view and FIGS. 5B and 5C are cross-sectional views of another electrophoresis device 101 with first and second constrictions 109a and 109b. The first constriction 109a is generally similar to that shown in FIG. 4A, and the second constriction 109b is generally similar to that shown in FIG. 3A. In further embodiments, the electrophoresis device 101 can also include three, four, or any suitable number of constrictions with cross-sectional area reduction in one dimension or two-dimensions.

Certain experiments were conducted to test the efficacy of ITP analysis in a microchannel with reduction in cross-sectional area. In the experiments, an electrophoresis device generally similar to that shown in FIG. 1A was used. As discussed in more detail below, by performing ITP in a cross-sectional area reducing microchannel, concentration factors greater than 10,000 were achieved.

Chemicals Used in Experiments

R-phycoerythrin (PE, MW=240,000 Da) was purchased from Molecular Probes of Eugene, Oreg. Potassium acetate, polyvinylpyrrolidone K-90 (PVP, MW=360,000 Da), urea, terrific broth (TB), carbenicillin, Triton X-100, sodium azide (NaN$_3$), phenylmethylsulphonylfluoride (PMSF), benzamidine, ammonium sulfate ((NH$_4$)$_2$SO$_4$), citric acid, dithiothreitol (DTT), ethylenediaminetetraacetic acid, β-mercaptoethanol sodium chloride (NaCl), potassium chloride (KCl), potassium phosphate (KH$_2$PO$_4$), and disodium phosphate (Na$_2$HPO$_4$) were purchased from Sigma-Aldrich of St. Louis, Mo. Pacific Blue™ C5-maleimide was purchased from Molecular Probes of Carlsbad, Calif.

Human cTnI (HcTnI) encoding gene was subcloned into expression vector pET3d. The resultant plasmid pET3d- hcTnI was transformed into OneShot® BL21 Star™ (DE3) Chemically Competent *E. coli* cells. The cells were grown on Luria Broth (LB) medium agar plates supplemented with 50 µg/mL of carbenicillin at 37° C. overnight. Several colonies were picked up and inoculated into 15 mL LB-carbenicillin liquid medium and shaken at 37° C. until $OD_{600}$ is up to 0.8~1. The pre-culture was inoculated into 2 L TB medium with 50 µg/mL carbenicillin. After shaking at 37° C. for 18 hours, the cells were spun down at 7,000×g for 10 min.

Preparation of cTnI

Cell pellets were suspended in a carboxy methyl (CM) buffer (6 M urea, 30 mM citric acid, 1 mM EDTA, and 1 mM DTT) with 0.01% Triton X-100, 0.01% $NaN_3$, 2 mM PMSF and 2 mM benzamidine and sonicated with a Misonix Sonicator® 3000 Ultrasonic Liquid Processor provided by Misonix Inc., Farmingdale, N.Y., on ice. The crude lysate was clarified by centrifugation at 40,000 G for 30 min. The supernatant was brought to 30% and 60% saturation with $(NH_4)_2SO_4$ sequentially, followed by stirring at 4° C. for 1 hour, and spun down at 28,000 G for 20 min. The supernatant was decanted and the pellet was re-suspended in 50 mL CM buffer. The solution was dialyzed against 1 L CM buffer overnight at 4° C. to remove residual $(NH_4)_2SO_4$. Next, the dialyzed and clarified supernatant was loaded onto an equilibrated CM sepharose (GE) column and an ÄKTA™ FPLC™ System (GE) was used to run gradient elution of NaCl concentration increasing from 0 to 0.3 M. The potential cTnI peak fractions were collected and SDS-PAGE was performed to evaluate the purity of the cTnI fractions.

Labeling of cTnI

Phosphate buffer saline (PBS) was prepared using NaCl, KCl, $Na_2HPO_4$, and $KH_2PO_4$ to pH 7.4, and 1.5 mL of purified cTnI was dialyzed three times in 1 L solutions of PBS 7.4 with 4 M urea for at least 8 hours at 4° C. in a 10,000 MWCO Slide-A-Lyzer Dialysis Cassette provided by Piercenet of Rockford, Ill. After dialysis, the cTnI was labeled with Pacific Blue™ C5-maleimide according to the manufacturer's instructions. Pacific Blue™ C5-maleimide is a UV fluorescent, thiol-reactive probe that readily reacts with the two cysteine groups on the cTnI molecule. A 10× molar excess of dye was mixed with the cTnI and allowed to react at 4° C. overnight. An excess of β-mercaptoethanol was added to quench the reaction. The labeled cTnI was again dialyzed as mentioned previously to remove excess dye. A Beckman Coulter DU 730 UV/Vis spectrophotometer provided by Beckman Coulter, Inc., of Brea, Calif., was used to determine the final protein concentration and the degree of labeling. The final protein concentration of cTnI was 0.46 mg/mL and the degree of labeling was about 2. The cTnI isoelectric point was checked by running isoelectric focusing PAGE (IEF-PAGE).

Electrolyte Solutions

An LE solution was prepared by adjusting pH of 20 mM potassium acetate solution to pH 4.5 with 10% (v/v) acetic acid. A TE solution includes 10 mM acetic acid at pH 3.8. PVP at 1% (w/v) was added to both LE and TE in order to suppress electro-osmotic flow. PE and labeled cTnI stock solutions were diluted in LE solution to concentrations of 4.0 µg/mL and 2.3 µg/mL, respectively. All electrolyte solutions were made up using nano-pure water. Electrolyte solutions were degassed with a vacuum pump.

Experimental Setup

Figure 6:
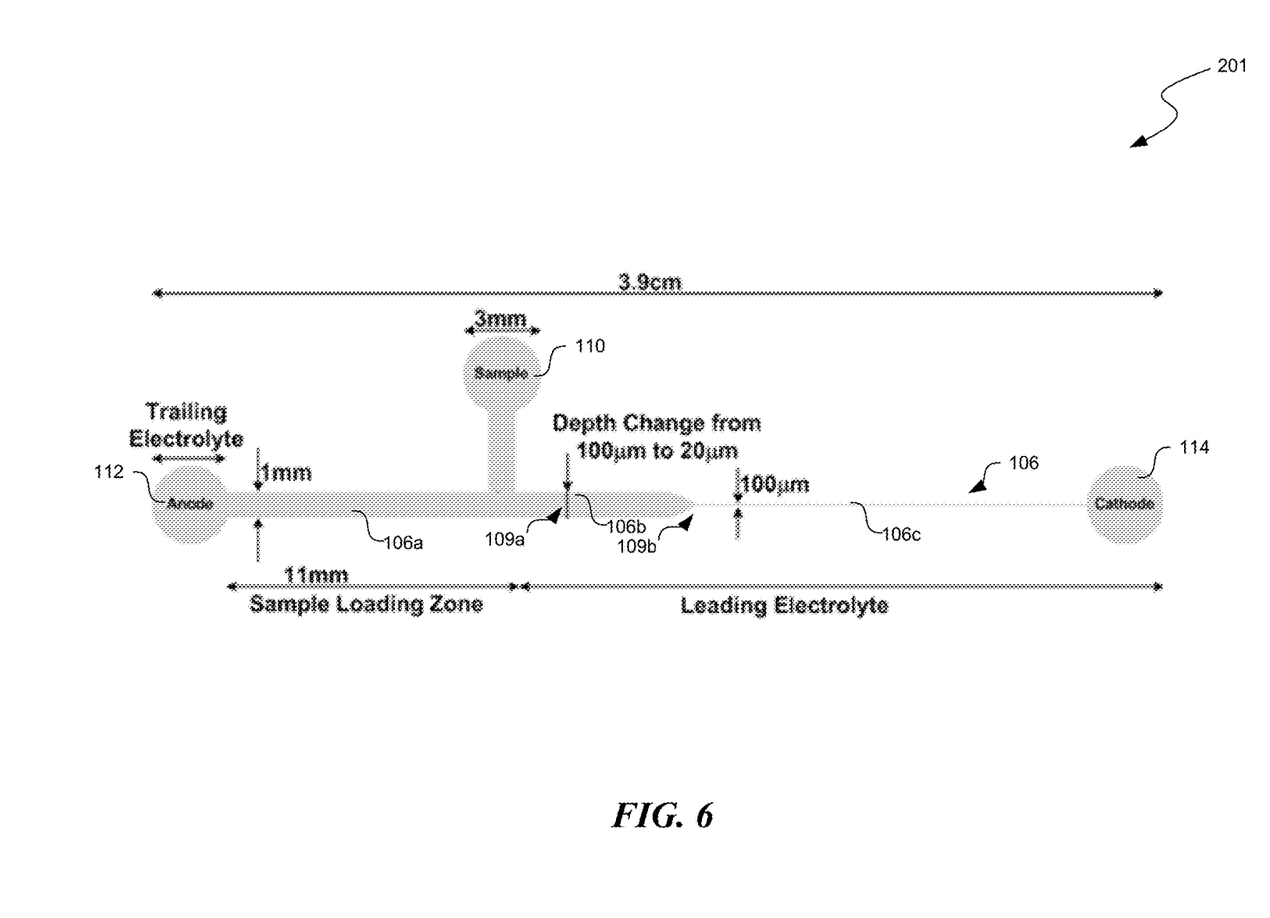
FIG. 6 is a plan view of an electrophoresis device showing dimensions for use in experiments in accordance with embodiments of the present technology.

FIG. 6 is a plan view of an electrophoresis device 201 used in the experiments with certain dimensions shown. As shown in FIG. 6, the electrophoresis device 201 is generally similar to the electrophoresis device 101 shown in FIG. 1A. As such, identical reference numbers identify similar elements or acts.

During testing, the electrophoresis device 201 was initially filled with the LE from the cathode reservoir 114 to the anode reservoir 112 using a 3 mL disposable syringe. Next, diluted PE and labeled cTnI in LE were introduced into the sample reservoir 110 and filled towards the anode reservoir 112 so that LE occupying the region between the sample reservoir 110 and anode reservoir 112 was washed out of the anode reservoir 112. At this point, the sample solution occupied the region between the sample reservoir 110 and the anode reservoir 112. The total mass load ($M_i$) of both PE and cTnI injected into the passage may be calculated by multiplying the initial concentration by the volume of the sample loading zone (1.1 µL). Next, the anode reservoir 112 was rinsed several times with TE and then filled with TE.

The filled electrophoresis device 201 was placed underneath a 5× objective lens of a Leica DM 2000 fluorescence microscope equipped with a DFC310 digital color camera provided by Leica Microsystems Inc., Bannockburn, Ill. The camera was controlled with the provided Leica Application Suite (LAS) V3.6 software to collect images of fluorescent proteins as the proteins migrated through the first channel 106 via ITP. The exposure time was set to 67.7 millisecond and the gain was set to 4.1×. The fluorescent proteins were excited with a Leica Microsystems EL 6000 light source using an A type filter cube. Platinum electrodes were submerged in the anode reservoir 112 and cathode reservoir 114 while the sample reservoir 110 was left to float.

Initially, the anode reservoir 112 was grounded and the cathode reservoir 114 was set to 400 V. After the proteins migrate from the first section 106a into the second section 106b, the voltage on the cathode reservoir 114 was reduced to 100 V. Representative images at the end of each experiment were collected. Electropherogram of the images were obtained for further analysis.

Results and Discussion

Potassium ion was chosen as the LE ion. Hydronium ion was chosen as the TE ion. The initial mass load ($M_i$) was calculated from the following equation $$M_i = c_i^0 \cdot L \cdot A \qquad \text{Equation 2}$$

where $c_i^0$ is the initial concentration of protein i (4.0 µg/mL for PE and cTnI, respectively), L is the length of sample loading zone (11 mm), and A is the cross-sectional area of the first channel 106 (0.1 $mm^2$). Thus, the total mass for PE and cTnI was 4.40 and 2.53 ng, respectively.

Figure 7:
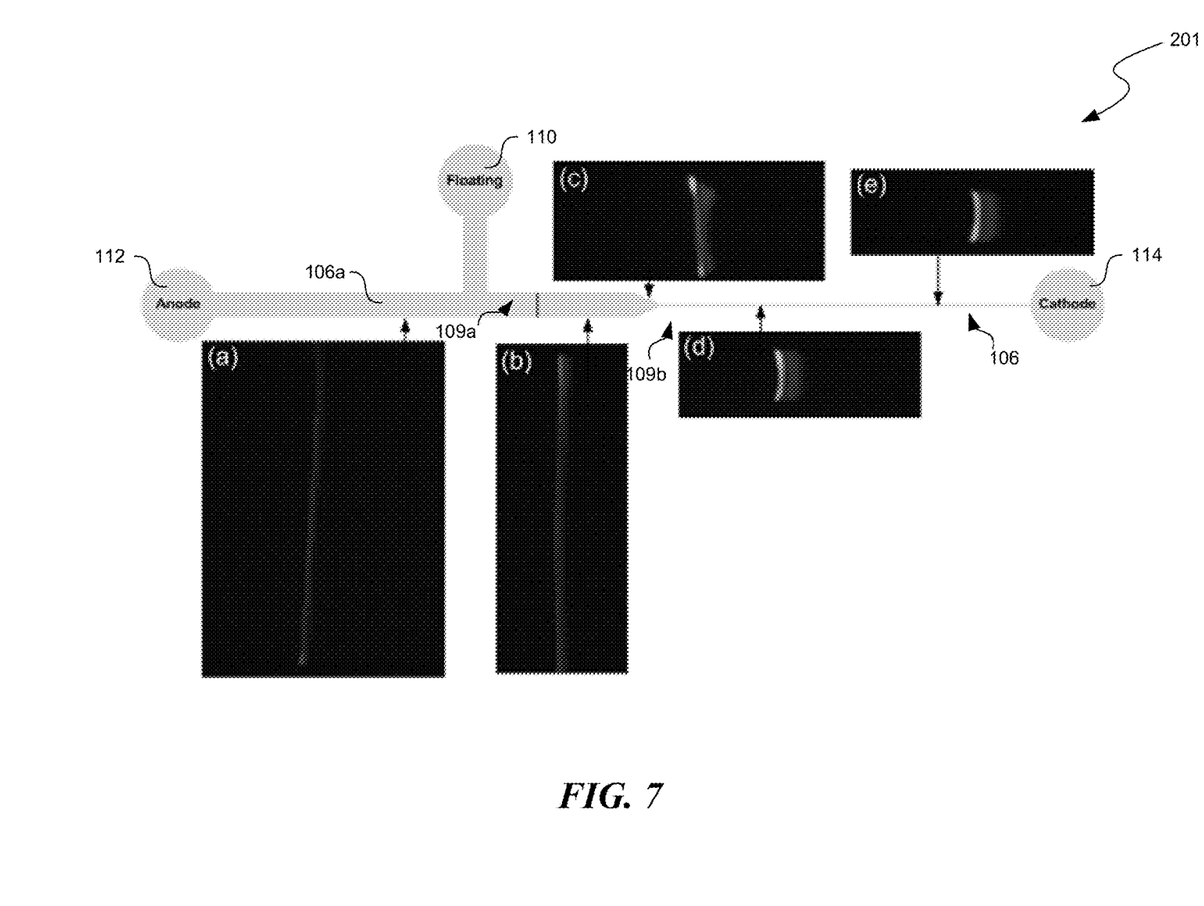
FIG. 7 shows stacking of labeled cTnI at different locations in the electrophoretic device in FIG. 6 during experiments conducted in accordance with embodiments of the present technology.

FIG. 7 shows stacking of labeled cTnI at different locations in the electrophoretic device 201 in FIG. 6 during experiments. As shown in FIG. 7, the proteins were not visualized until just before first constriction 109a. At the running pH, cTnI ran ahead of PE because cTnI had a higher effective electrophoretic mobility. The proteins continued to collect mass through the sample loading zone and the intensity of the fluorescence increased as they migrated through the first constriction 109a. Prior to the second constriction 109b, the voltage on the cathode was reduced from 400 to 100V. An image was collected prior to protein bands migration into the cathode reservoir 114 clearly demonstrating ITP stacking of labeled cTnI and PE into nearly pure and distinct zones.

Figure 8:
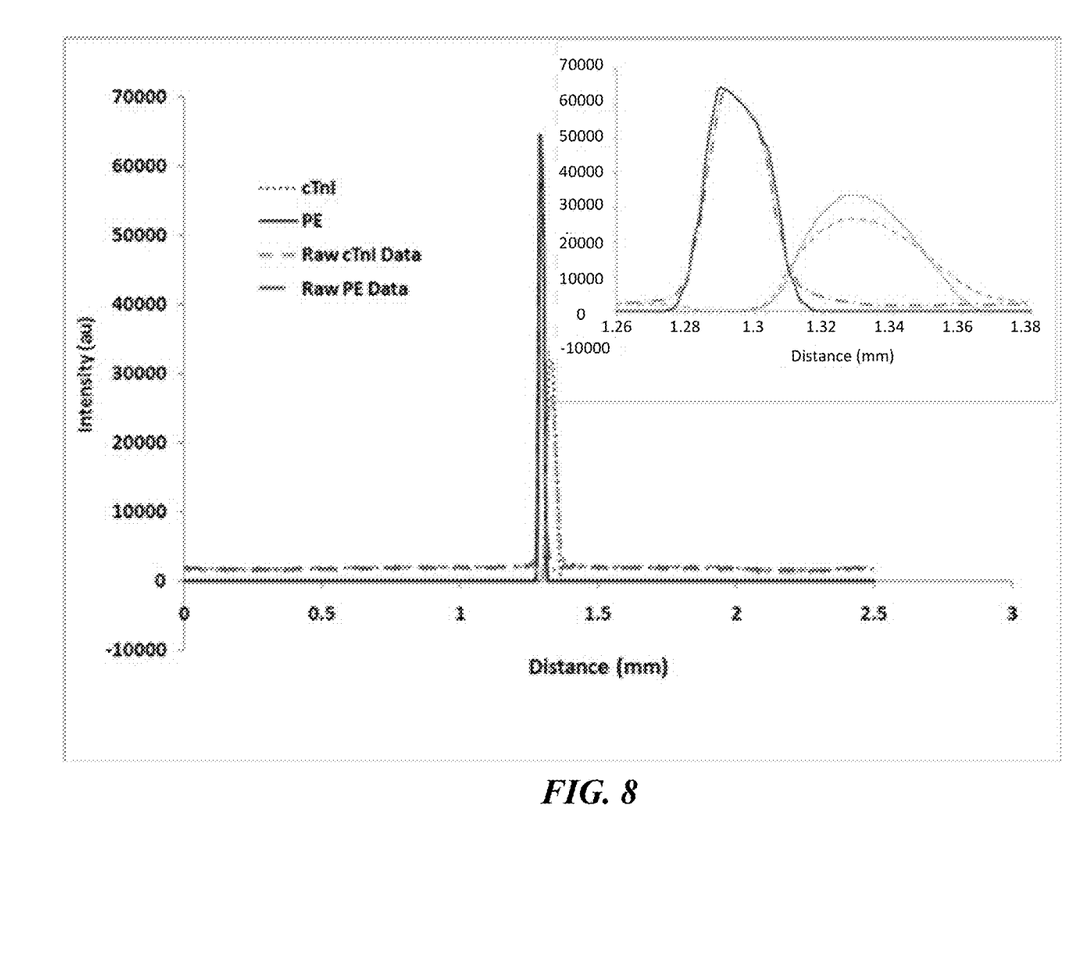
FIG. 8 is an electropherogram of test results based on experiments conducted in accordance with embodiments of the present technology.

After several runs, electropherograms were obtained by plotting distance (mm) relative to the field of view of the camera versus average intensity over the entire width of the first channel 106 for each protein. FIG. 8 shows an example electropherogram including both raw and modified data with an inset showing an enlarged plot of protein peaks. Using moment analysis, the peak width of each protein can be determined from the data. Subsequent concentrations and concentration factors for each protein were then calculated based on the electropherograms. A summary of the experimental peak widths determined from the moment analysis, final concentrations from Equation 1, and concentration factors for PE and cTnI are shown in the table below.

|  | PE | | | cTnI | | |
|---|---|---|---|---|---|---|
| Trial # | Peak width (μm) | Concentration (mg mL$^{-1}$) | Concentration Factor | Peak width (μm) | Concentration (mg mL$^{-1}$) | Concentration Factor |
| 1 | 30.21 | 72.84 | 18,210 | 50.83 | 24.89 | 10,822 |
| 2 | 35.58 | 62.18 | 15,545 | 51.21 | 24.70 | 10,739 |
| 3 | 29.45 | 74.70 | 18,675 | 46.93 | 26.96 | 11,722 |
| Average | 31.68 | 69.91 | 17,477 | 49.66 | 25.52 | 11,094 |
| St. Dev. | 3.23 | 6.76 | 1,689 | 2.37 | 1.25 | 545 |

As clearly shown in the table above, an average concentration factor of 17,477 was achieved in three trials.

From the foregoing, it will be appreciated that specific embodiments of the disclosure have been described herein for purposes of illustration, but that various modifications may be made without deviating from the disclosure. In addition, many of the elements of one embodiment may be combined with other embodiments in addition to or in lieu of the elements of the other embodiments. Accordingly, the technology is not limited except as by the appended claims.

I claim:

1. An electrophoresis device, comprising:
a first electrode having a first polarity;
a second electrode having a second polarity opposite the first polarity;
a substrate including a channel configured to contain a sample, the channel having a first section and a second section between a first end and a second end, the first end being electrically coupled to the first electrode and the second end being electrically coupled to the second electrode, wherein:
the first section has a first cross-sectional area at a first edge;
the second section has a second cross-sectional area at a second edge abutting the first edge of the first section;
the first cross-sectional area is greater than the second cross-sectional area in at least one of a first dimension or in a second dimension orthogonal to the first dimension;
the first and second electrodes are configured to apply an electric voltage on the sample in the channel, thereby forcing components of the sample to migrate from the first end of the channel toward the second end; and
the second section of the channel is configured to separate and concentrate the components in the sample under the influence of the applied electric voltage, wherein:
the second edge is a second inlet edge opposite a second outlet edge of the second section;
the channel further includes a third section with a third cross-sectional area at a third edge abutting the second outlet edge of the second section;
the second cross-sectional area is greater than the third cross-sectional area;
a first reduction from the first cross-sectional area to the second cross-sectional area is in the first dimension and second dimension;
a second reduction from the second cross-sectional area to the third cross-sectional area is also in the first dimension and the second dimension.

2. The electrophoresis device of claim 1 wherein the first reduction in the first dimension and the second reduction in the second dimension are concomitant with each other.

3. The electrophoresis device of claim 1 wherein:
the first reduction and the second reduction are both about 10:1.

4. The electrophoresis device of claim 1 wherein:
the first reduction and the second reduction are both about 10:1;
the channel is a first channel; and
the electrophoresis device further includes:
a second channel in fluid communication with the first section of the first channel;
a first reservoir proximate the first end, the first reservoir being configured to store a trailing electrolyte;
a second reservoir proximate the second end, the second reservoir being configured to store a leading electrolyte; and
a sample reservoir in fluid communication with the second channel, the sample reservoir being configured to store a sample having components with an electrophoretic mobility higher than that of the trailing electrolyte and lower than that of the leading electrolyte.

5. The electrophoresis device of claim 1 wherein at least the second section of the channel is a microchannel.

6. An electrophoresis device, comprising:
a first electrode having a first polarity;
a second electrode having a second polarity opposite the first polarity; and
a substrate having a channel configured to carry one or more fluids therein, the channel having a first end and a second end spaced apart from the first end, wherein the first and second ends of the channel are electrically coupled to the first and second electrodes, respectively, and wherein:
the channel includes a constriction separating a first section and a second section between the first and second ends, the first section having a first cross-sectional area at a first edge and the second section having a second cross-sectional area at a second edge abutting the first edge of the first section at the constriction, the second cross-sectional area being smaller than the first cross-sectional area;
the first and second electrodes are configured to apply an electric voltage on the one or more fluids in the channel, thereby forcing components of the one or more fluids to migrate from the first end of the channel toward the second end; and
the first and second sections of the channel are configured to separate and concentrate components in the one or more fluids under the influence of the applied electric voltage, wherein:

the channel extends between the first and second ends along a first direction; and the constriction includes a reduction in cross-sectional area from the first cross-sectional area of the first section to the second cross-sectional area of the second section along a second direction and a third direction both perpendicular to the first direction.

7. The electrophoresis device of claim 6 wherein:
the constriction is a first constriction;
the channel further includes a second constriction;
the channel extends between the first and second ends along a first direction; and
the first constriction includes:
  a first reduction in cross-sectional area along a second direction perpendicular to the first direction; and
  the second constriction includes a second reduction in cross-sectional area along a third direction perpendicular to the first direction, the first and second reductions being spaced apart from each other along the first direction.

8. The electrophoresis device of claim 6 wherein:
the constriction is a first constriction;
the channel further includes a second constriction;
the first constriction includes a first reduction in cross-sectional area between the first and second ends; and
the second constriction includes a second reduction in cross-sectional area between the first and second ends, the first and second reductions being spaced apart from each other along a flow direction of the channel.

9. The electrophoresis device of claim 6 wherein:
the constriction is a first constriction;
the channel further includes a second constriction;
the first constriction includes a first reduction in cross-sectional area between the first and second ends along a direction; and
the second constriction includes a second reduction in cross-sectional area between the first and second ends along another direction perpendicular to the direction, the first and second reductions being spaced apart from each other.

10. The electrophoresis device of claim 6 wherein the constriction includes:
  a first reduction in cross-sectional area between the first and second ends along a direction; and
  a second reduction in cross-sectional area between the first and second ends along another direction perpendicular to the direction, the first and second reductions being concomitant with each other.

11. The electrophoresis device of claim 6 wherein:
the constriction is a first constriction;
the channel further includes a second constriction;
the first constriction includes a first reduction in cross-sectional area between the first and second ends along multiple directions; and
the second constriction includes a second reduction in cross-sectional area between the first and second ends along the multiple directions, the first and second reductions being spaced apart from each other along a flow direction of the channel.

12. An electrophoresis device, comprising:
a first electrode having a first polarity;
a second electrode having a second polarity opposite the first polarity; and
a substrate having a channel configured to carry one or more fluids therein, the channel having a first end and a second end spaced apart from the first end, wherein the first and second ends of the channel are electrically coupled to the first and second electrodes, respectively, and wherein:

the channel includes a constriction separating a first section and a second section between the first and second ends, the first section having a first cross-sectional area at a first edge and the second section having a second cross-sectional area at a second edge abutting the first edge of the first section at the constriction, the second cross-sectional area being smaller than the first cross-sectional area;

the first and second electrodes are configured to apply an electric voltage on the one or more fluids in the channel, thereby forcing components of the one or more fluids to migrate from the first end of the channel toward the second end; and the first and second sections of the channel are configured to separate and concentrate components in the one or more fluids under the influence of the applied electric voltage, wherein:
the constriction is a first constriction;
the channel further includes a second constriction;
the first constriction includes a first reduction in cross-sectional area between the first and second ends along multiple directions; and
the second constriction includes a second reduction in cross-sectional area between the first and second ends along the multiple directions, the first and second reductions being spaced apart from each other along a flow direction of the channel.

13. The electrophoresis device of claim 12 wherein:
the channel extends between the first and second ends along a first direction; and
the first constriction includes:
  a first reduction in cross-sectional area along a second direction perpendicular to the first direction; and
  the second constriction includes a second reduction in cross-sectional area along a third direction perpendicular to the first direction, the first and second reductions being spaced apart from each other along the first direction.

14. The electrophoresis device of claim 12 wherein the first constriction and the second constriction are concomitant with each other.

15. The electrophoresis device of claim 12 wherein:
the first reduction and the second reduction are both about 10:1.

16. The electrophoresis device of claim 12 wherein:
the first reduction and the second reduction are both about 10:1;
the channel is a first channel; and
the electrophoresis device further includes:
  a second channel in fluid communication with the first section of the first channel;
  a first reservoir proximate the first end, the first reservoir being configured to store a trailing electrolyte;
  a second reservoir proximate the second end, the second reservoir being configured to store a leading electrolyte; and
  a sample reservoir in fluid communication with the second channel, the sample reservoir being configured to store a sample having components with an electrophoretic mobility higher than that of the trailing electrolyte and lower than that of the leading electrolyte.

17. The electrophoresis device of claim 12 wherein at least the second section of the channel is a microchannel.

* * * * *